(12) United States Patent
Enomoto (10) Patent No.: US 11,980,340 B2
(45) Date of Patent: May 14, 2024

(54) ENDOSCOPE APPARATUS AND METHOD OF CONTROLLING ENDOSCOPE

(71) Applicant: OLYMPUS CORPORATION, Tokyo (JP)

(72) Inventor: Kengo Enomoto, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 519 days.

(21) Appl. No.: 17/158,074

(22) Filed: Jan. 26, 2021

(65) Prior Publication Data

US 2021/0145264 A1 May 20, 2021

Related U.S. Application Data

(63) Continuation of application No. PCT/JP2019/008243, filed on Mar. 1, 2019.

(30) Foreign Application Priority Data

Jul. 30, 2018 (JP) .................................. 2018-142419

(51) Int. Cl.
*A61B 1/00* (2006.01)
*A61B 1/045* (2006.01)
*A61B 1/05* (2006.01)

(52) U.S. Cl.
CPC ...... *A61B 1/00096* (2013.01); *A61B 1/00009* (2013.01); *A61B 1/00018* (2013.01); *A61B 1/045* (2013.01); *A61B 1/05* (2013.01)

(58) Field of Classification Search
CPC ............ A61B 1/00096; A61B 1/00009; A61B 1/00018; A61B 1/045; A61B 1/05; A61B 1/00; A61B 1/00188

(Continued)

(56) References Cited

U.S. PATENT DOCUMENTS 4,905,668 A * 3/1990 Ohsawa ............. A61B 1/00059
600/109
5,282,045 A * 1/1994 Mimura ............... H04N 13/236
348/E5.045

(Continued)

FOREIGN PATENT DOCUMENTS

| JP | 2000-047090 A | 2/2000 |
|---|---|---|
| JP | 2008-068021 A | 3/2008 |
| JP | 2018-031981 A | 3/2018 |

OTHER PUBLICATIONS

International Search Report dated May 14, 2019 issued in PCT/JP2019/008243.

*Primary Examiner* — Timothy J Neal
*Assistant Examiner* — James Edward Boice
(74) *Attorney, Agent, or Firm* — Scully, Scott, Murphy & Presser, P.C.

(57) ABSTRACT

An endoscope apparatus includes: an endoscope distal end portion including an optical system configured to form an optical image, an image sensor configured to generate an image signal in accordance with a predetermined frame rate when the optical image is input, and an actuator configured to move the optical system along an optical axis; and a controller electrically connected to the endoscope distal end portion and including an imaging circuit configured to acquire the image signal from the image sensor, a drive circuit configured to feed a drive voltage to the actuator, and a processor configured to control the imaging circuit and the drive circuit, detect a vertical blanking period of the image signal acquired by the imaging circuit based on the image signal, and control the drive circuit to gradually increase a voltage supplied to the actuator within the vertical blanking period.

13 Claims, 6 Drawing Sheets

(58) Field of Classification Search
USPC .................................... 600/109, 176, 167
See application file for complete search history.

(56) References Cited

U.S. PATENT DOCUMENTS

| | | | |
|---|---|---|---|
| 2004/0097791 A1* | 5/2004 | Tokuda | A61B 1/00183 600/173 |
| 2007/0055099 A1* | 3/2007 | Kimoto | A61B 1/041 600/109 |
| 2008/0177137 A1 | 7/2008 | Matsui | |
| 2015/0334289 A1* | 11/2015 | Yoshino | H04N 23/673 348/353 |
| 2016/0198076 A1* | 7/2016 | Fujimoto | H04N 23/673 348/68 |
| 2016/0377855 A1* | 12/2016 | Takata | G02B 23/2438 359/696 |
| 2018/0059509 A1 | 3/2018 | Naka | |

\* cited by examiner

ENDOSCOPE APPARATUS AND METHOD OF CONTROLLING ENDOSCOPE

This application is a continuation of PCT international application No. PCT/JP2019/008243 filed on Mar. 1, 2019, which designates the United States, incorporated herein by reference, and which claims the benefit of priority from Japanese Patent Application No. 2018-142419, filed on Jul. 30, 2018, incorporated herein by reference.

BACKGROUND

The present disclosure relates to an endoscope apparatus an a method of controlling an endoscope.

There is a known technique of an endoscope apparatus that includes, in a distal end portion, an image sensor and an actuator that changes the focal length of an optical system so as to change the focal length of the optical system due to the driving of the actuator (see Japanese Laid-open Patent Publication No. 2008-68021). According to this technique, the image signal generated by the image sensor and the control signal for driving the actuator are transmitted from the endoscope apparatus to a processor via a common signal line, and the control signal is transmitted to the endoscope apparatus during a blanking period of the image signal to drive the actuator.

SUMMARY

According to one aspect of the present disclosure, there is provided an endoscope apparatus including: an endoscope distal end portion including an optical system configured to form an optical image, an image sensor configured to generate an image signal in accordance with a predetermined frame rate when the optical image is input, and an actuator configured to move the optical system along an optical axis; and a controller electrically connected to the endoscope distal end portion via a transmission cable, the controller including an imaging circuit configured to acquire the image signal from the image sensor via the transmission cable, a drive circuit configured to feed a drive voltage to the actuator via the transmission cable, and a processor configured to control the imaging circuit and the drive circuit, detect a vertical blanking period of the image signal acquired by the imaging circuit based on the image signal, and control the drive circuit to gradually increase a voltage supplied to the actuator within the vertical blanking period.

According to another aspect of the present disclosure, there is provided a method of controlling an endoscope including an imaging circuit configured to generate an image signal of a subject from an optical image input via an optical system, an actuator configured to move the optical system along an optical axis, and a drive circuit configured to supply a drive voltage to the actuator, the method including: detecting a vertical blanking period of the image signal output from the imaging circuit; and during the vertical blanking period, gradually increasing the drive voltage supplied to the actuator when the actuator is to be driven.

According to still another aspect of the present disclosure, there is provided an endoscope apparatus including: an endoscope distal end portion including an optical system configured to form an optical image, an image sensor configured to generate an image signal in accordance with a predetermined frame rate when the optical image is input, and an actuator configured to move the optical system along an optical axis; and a controller electrically connected to the endoscope distal end portion via a transmission cable, the controller including an imaging circuit configured to acquire the image signal from the image sensor via the transmission cable, a drive circuit configured to supply a drive signal to the actuator via the transmission cable, and a processor configured to control the imaging circuit and the drive circuit, detect a vertical blanking period of the image signal acquired by the imaging circuit based on the image signal, and control the drive circuit to gradually increase the drive signal within the vertical blanking period.

The above and other features, advantages and technical and industrial significance of this disclosure will be better understood by reading the following detailed description of presently preferred embodiments of the disclosure, when considered in connection with the accompanying drawings.

DETAILED DESCRIPTION

An endoscope apparatus including an endoscope having an image sensor in a distal end portion on a distal end side of an insertion portion inserted into a subject is described below as modes (hereinafter referred to as "embodiments") for carrying out the present disclosure. Further, the present disclosure is not limited to the embodiments. In the drawings, the same parts are denoted by the same reference numeral. It should be noted that the drawings are schematic and the relationship between the thickness and the width of each member, the ratio of each member, and the like, are different from those in reality. The drawings include portions having different dimensions or proportions from each other.

Figure 1:
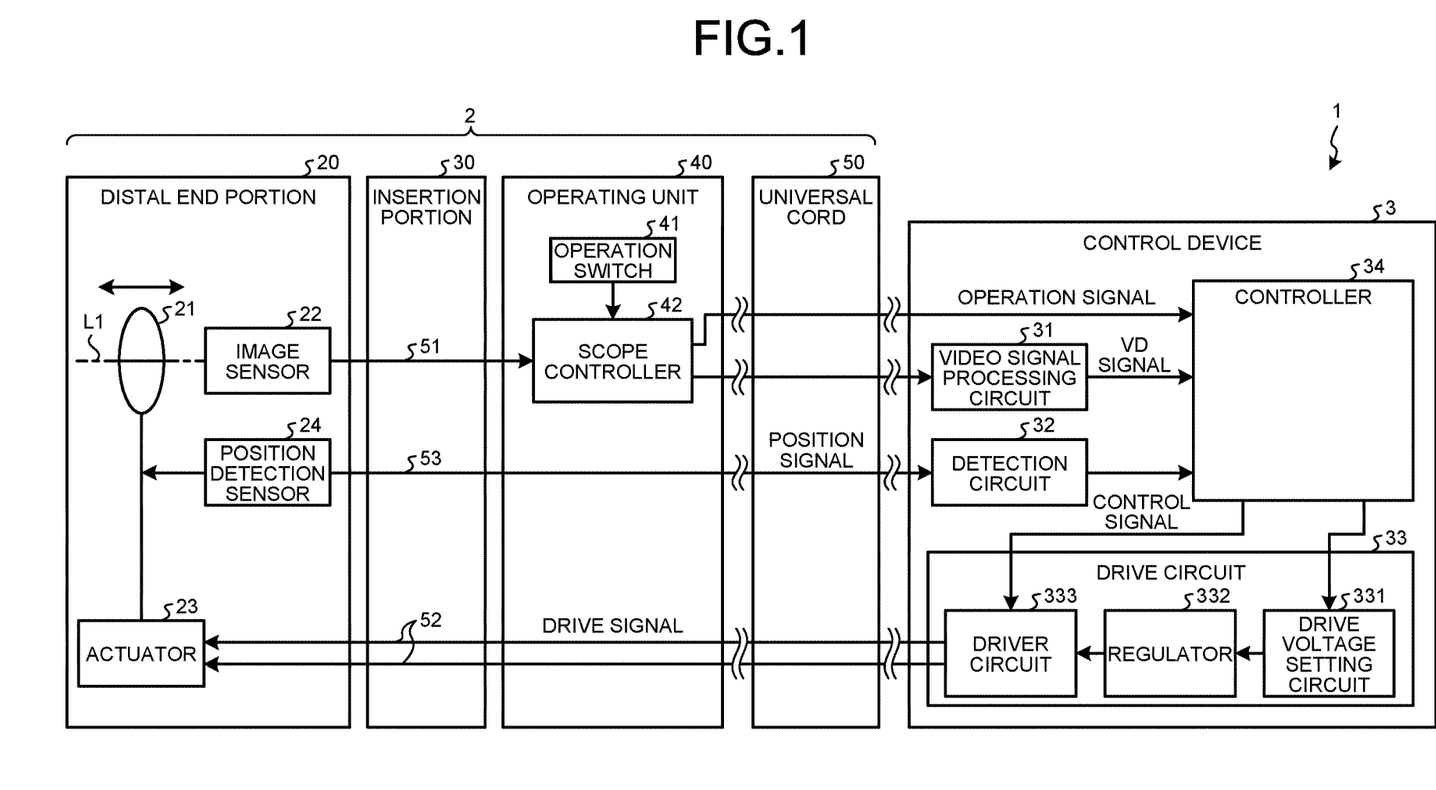
FIG. 1 is a block diagram illustrating a functional configuration of an endoscope apparatus according to a first embodiment.

FIG. 1 is a block diagram illustrating a functional configuration of an endoscope apparatus according to a first embodiment. An endoscope apparatus 1 illustrated in FIG. 1 includes at least an endoscope 2 and a control device 3. In the endoscope apparatus 1 illustrated in FIG. 1, the endoscope 2 is inserted into the body cavity of the subject to capture the inside of the body of the subject so as to generate an image signal. In the endoscope apparatus 1, the control device 3 performs various types of signal processing on the image signal input from the endoscope 2 and outputs the signal to a display device (not illustrated).

The endoscope 2 includes a distal end portion 20, an insertion portion 30, an operating unit 40, and a universal cord 50. With the endoscope 2, the insertion portion 30 including the distal end portion 20 provided on the distal end side of the insertion portion 30 is inserted into the body cavity of the subject. The endoscope 2 captures the image of the inside of the body of the subject to generate an image signal. The endoscope 2 outputs an image signal generated by the distal end portion 20 to the control device 3 via the insertion portion 30 and the universal cord 50.

The distal end portion 20 includes an optical system 21, an image sensor 22, an actuator 23, and a position detection sensor 24.

The optical system 21 is configured by using one or more lenses, etc. The optical system 21 is provided in the distal end portion 20 so as to be movable in the direction of an optical axis L1 The optical system 21 changes the focal length in accordance with the drive of the actuator 23.

The image sensor 22 generates an image signal in accordance with a predetermined frame rate when an optical image formed by the optical system 21 is input on the basis of a control signal input from the control device 3 via a first transmission cable 51 that is wired into the insertion portion 30, the operating unit 40, and the universal cord 50. The image sensor 22 outputs an image signal to the control device 3 via the first transmission cable 51. The image sensor 22 is configured by using a complementary metal oxide semiconductor (CMOS) or a charge coupled device (CCD) image sensor, or the like.

The actuator 23 is driven based on a drive signal input from the control device 3 via a second transmission cable 52 wired into the insertion portion 30, the operating unit 40, and the universal cord 50. The actuator 23 is configured by using a magnetic member, or the like, including a coil and the optical system 21 and having a tubular shape. The actuator 23 generates a magnetic field when the drive signal input from the control device 3 via the second transmission cable 52 flows through the coil so that the magnetic field moves the magnetic member along the direction of the optical axis toward the wide-angle side or the telescopic side. Accordingly, the focal length of the optical system 21 changes. The actuator 23 may use a voice coil motor or may be configured by using a shape-memory alloy so as to change its shape due to the application of a drive signal.

The position detection sensor 24 detects the position of the optical system 21 on the optical axis and outputs the detection result to the control device 3 via a third transmission cable 53. The position detection sensor 24 is configured by using, for example, a Hall element, an encoder, or the like.

The distal end side of the insertion portion 30 is coupled to the distal end portion 20, and the proximal end side of the insertion portion 30 is coupled to the operating unit 40. The insertion portion 30 includes at least the first transmission cable 51, the second transmission cable 52, the third transmission cable 53, and a light guide (not illustrated). The first transmission cable 51, the second transmission cable 52, the third transmission cable 53, and the light guide (not illustrated) are connected to one another in parallel in the insertion portion 30 and the universal cord 50.

The first transmission cable 51 electrically connects the image sensor 22 and the control device 3 to transmit a control signal from the control device 3 to the image sensor 22 and transmit an image signal from the image sensor 22 to the control device 3.

The second transmission cable 52 electrically connects the actuator 23 and the control device 3 to transmit a drive signal from the control device 3 to the actuator 23 together with the ground.

The third transmission cable 53 electrically connects the position detection sensor 24 and the control device 3 to transmit the position signal indicating a detection result detected by the position detection sensor 24 from the position detection sensor 24 to the control device 3.

The operating unit 40 has various circuits installed therein to receive the input of operation signals of various operations regarding the endoscope 2. The operating unit 40 includes an operation switch 41 and a scope controller 42. One end side of the operating unit 40 is coupled to the insertion portion 30, and the other end side thereof is coupled to the universal cord 50.

The operation switch 41 is configured by using various switches, toggle switches, buttons, or the like, to output the operation signal corresponding to an operation from outside to the control device 3.

The scope controller 42 controls each unit of the endoscope 2 in an integrated manner. The scope controller 42 is configured by using, for example, a central processing unit (CPU) or a field programmable gate array (FPGA). The scope controller 42 performs predetermined signal processing, such as amplification processing, on an image signal input from the image sensor 22 and outputs the signal to the control device 3.

The universal cord 50 includes the first transmission cable 51, the second transmission cable 52, the third transmission cable 53, and the light guide (not illustrated). The universal cord 50 is detachably attached to the control device 3.

The control device 3 includes a video signal processing circuit 31, a detection circuit 32, a drive circuit 33, and a controller 34.

The video signal processing circuit 31 performs various kinds of signal processing, such as AD conversion processing or noise reduction processing, on an image signal input from the scope controller 42 via the first transmission cable 51 and outputs the signal to the controller 34. The video signal processing circuit 31 outputs, to the controller 34, a vertical synchronization signal (hereinafter simply referred to as "VD signal") and a horizontal synchronization signal included in an image signal input from the scope controller 42 via the first transmission cable 51. According to the first embodiment, the video signal processing circuit 31 functions as an imaging circuit.

The detection circuit 32 performs AD conversion processing on an analog position signal input from the position detection sensor 24 via the third transmission cable 53 and outputs the signal to the controller 34.

The drive circuit 33 supplies a drive signal for driving the actuator 23 provided in the distal end portion 20 of the endoscope 2 under the control of the controller 34. The drive circuit 33 supplies a drive signal to drive the actuator 23. The drive circuit 33 includes a drive voltage setting circuit 331, a regulator 332, and a driver circuit 333.

The drive voltage setting circuit 331 sets the drive voltage of the drive signal output from the regulator 332 under the control of the controller 34. The drive voltage setting circuit 331 is configured by using a D/A conversion circuit, a comparator circuit, etc.

The regulator 332 outputs, to the driver circuit 333, the drive signal obtained by adjusting the voltage of the DC power input from a DC power circuit (not illustrated) to the drive voltage set by the drive voltage setting circuit 331.

The driver circuit 333 outputs the drive signal input from the regulator 332 to the second transmission cable 52 under the control of the controller 34. The driver circuit 333 is configured by using an H-bridge circuit, etc.

The controller 34 controls each unit included in the endoscope apparatus 1 in an integrated manner. The controller 34 controls the drive signal supplied by the drive circuit 33 to the actuator 23 to adjust the position of the optical system 21 along the optical axis L1. Specifically, when the controller 34 causes the drive circuit 33 to output the drive signal in a case where an operation signal is input from the operation switch 41, the controller 34 performs control so as to cause the drive circuit 33 to gradually change and output the value of the drive signal, and causes the drive circuit 33 to gradually change the drive signal, supply the gradually changed drive signal, and complete the output of the drive signal within the blanking period of the image frame of the image signal.

Figure 2:
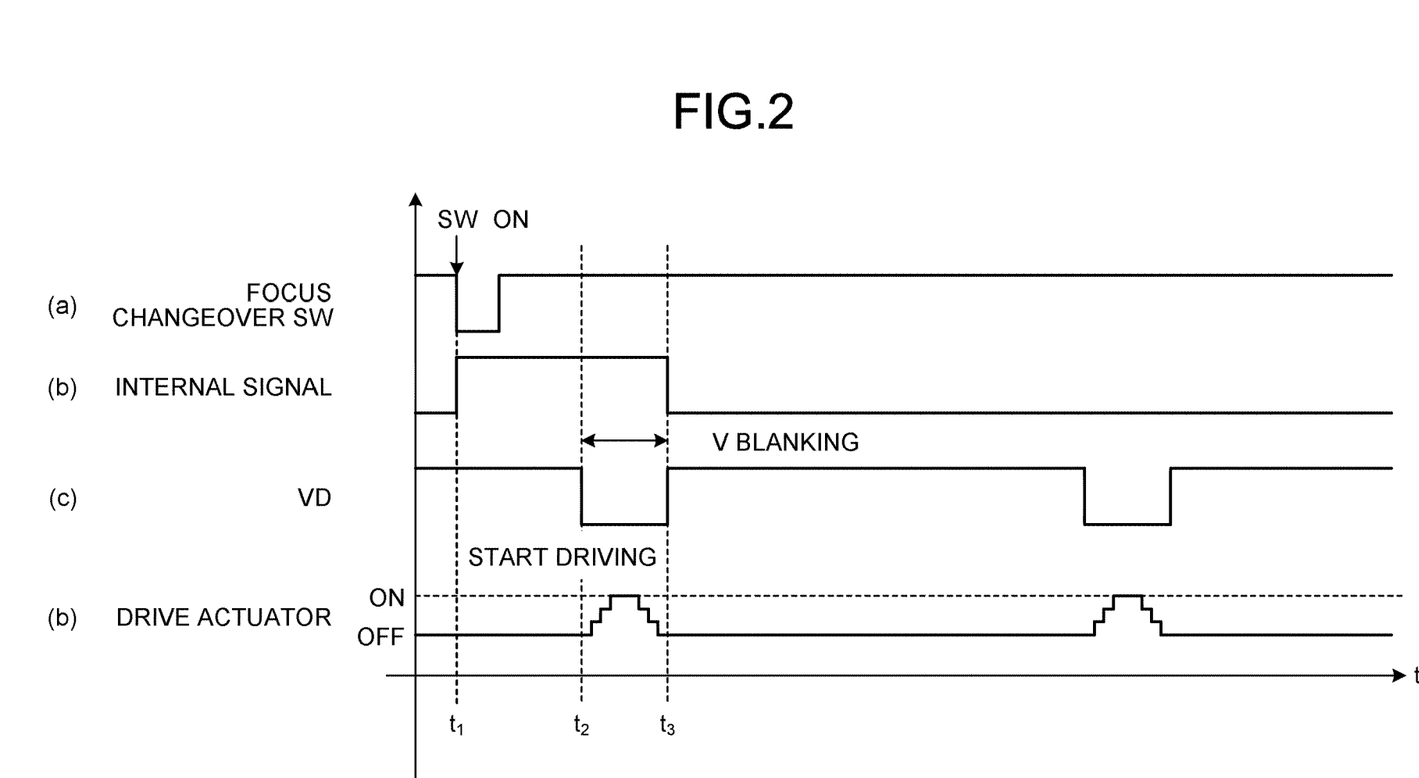
FIG. 2 is a timing chart illustrating an operation performed by the endoscope apparatus according to the first embodiment.

Next, operation processing of the endoscope apparatus 1 is described. FIG. 2 is a timing chart illustrating the overview of an operation performed by the endoscope apparatus 1. In FIG. 2, (a) denotes the timing when the operation switch 41 is pressed, (b) denotes the output timing of an operation signal, (c) denotes the timing of a vertical synchronization signal (VD), and (d) denotes a change in the drive signal of the actuator 23. In FIG. 2, the horizontal axis represents time.

As illustrated in FIG. 2, to cause the drive circuit 33 to supply a drive signal when an operation signal is input from the operation switch 41 (time $t_i$), the controller 34 causes the drive circuit 33 to gradually change the voltage value of the drive signal and supply the gradually changed drive signal within a blanking period (for example, from time $t_2$ to time $t_3$). Specifically, when the controller 34 causes the drive circuit 33 to gradually change the voltage value of the supplied drive signal, the controller 34 causes the drive circuit 33 to end the supplied drive signal within the blanking period. More specifically, the controller 34 controls the drive signal supplied by the drive circuit 33 such that the voltage value of the drive signal changes like a stepwise pulse and a stepwise change falls within a blanking period. In a case where the drive signal supplied by the drive circuit 33 has a large absolute value, the controller 34 causes the drive circuit 33 to gradually change the drive signal and supply the gradually changed drive signal; however, in a case where the drive signal supplied by the drive circuit 33 has a small absolute value, the controller 34 may cause the drive circuit 33 to instantaneously change the drive signal to zero.

Figure 3:
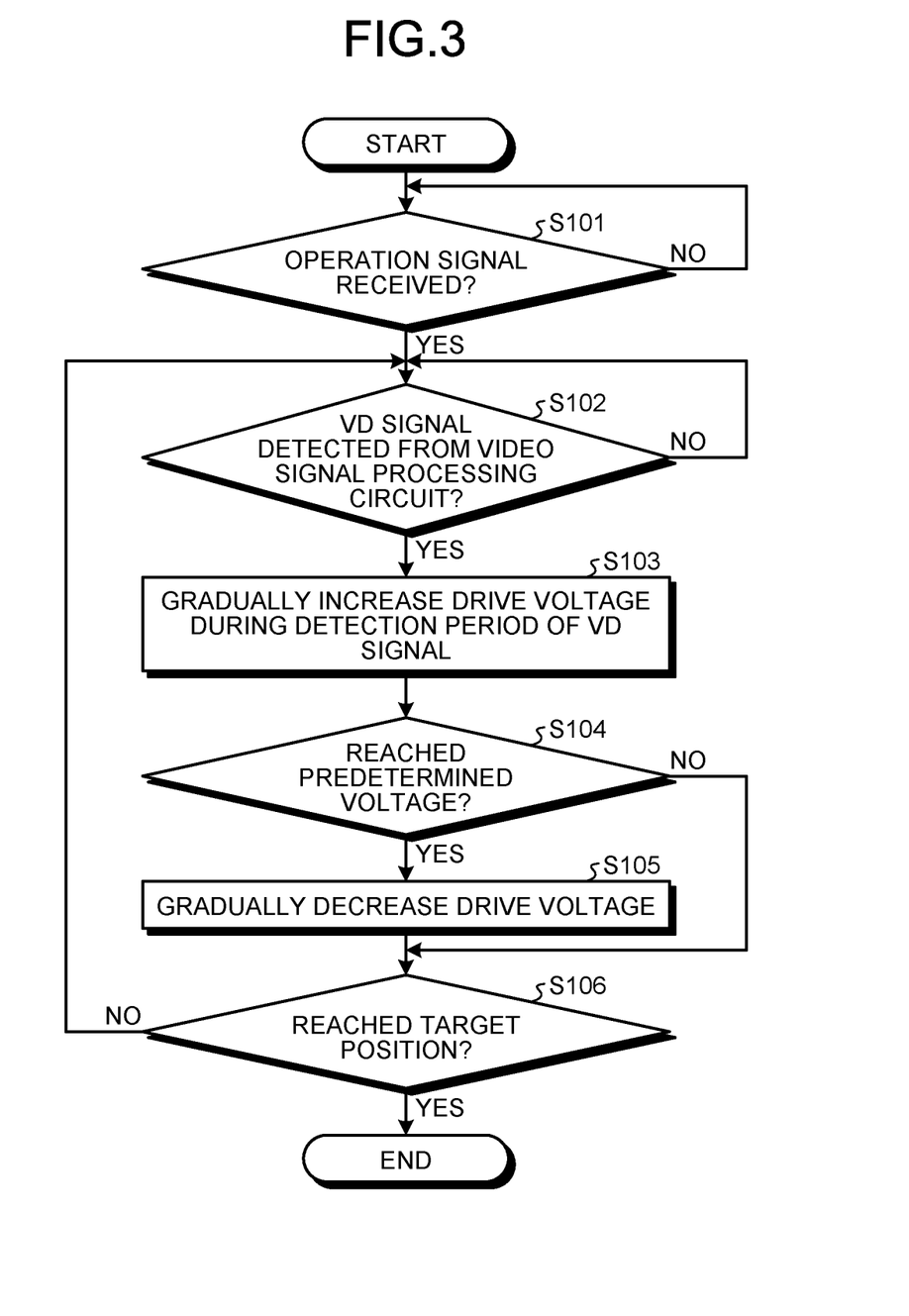
FIG. 3 is a flowchart illustrating the overview of a process performed by the endoscope apparatus according to the first embodiment.

Next, the overview of a process performed by the endoscope apparatus 1 is described. FIG. 3 is a flowchart illustrating the overview of the process performed by the endoscope apparatus 1.

As illustrated in FIG. 3, first, when an operation signal is received from the operation switch 41 of the endoscope apparatus 1 (Step S101: Yes), the endoscope apparatus 1 proceeds to Step S102 described below. Conversely, when no operation signal is received from the operation switch 41 of the endoscope apparatus 1 (Step S101: No), the endoscope apparatus 1 waits until an operation signal is received from the operation switch 41 of the endoscope apparatus 1.

At Step S102, when the controller 34 detects a VD signal from the video signal processing circuit 31 (Step S102: Yes), the endoscope apparatus 1 proceeds to Step S103 described below. Conversely, when the controller 34 detects no VD signal from the video signal processing circuit 31 (Step S102: No), the endoscope apparatus 1 waits until the controller 34 detects a VD signal from the video signal processing circuit 31.

At Step S103, the controller 34 causes the drive voltage of the drive signal output from the drive circuit 33 to be gradually increased during the detection period (blanking period) of the VD signal.

Subsequently, the controller 34 determines whether the drive voltage of the drive signal has reached a predetermined voltage (Step S104) and, when it is determined that the drive voltage of the drive signal has reached the predetermined voltage (Step S104: Yes), causes the drive voltage of the drive signal output from the drive circuit 33 to be gradually decreased (Step S105) so that the endoscope apparatus 1 proceeds to Step S106 described below. When it is determined that the drive voltage of the drive signal has not reached the predetermined voltage (Step S104: No), the endoscope apparatus 1 proceeds to Step S106 described below.

Then, the controller 34 determines whether the position of the optical system 21 has reached the target position based on the detection result input from the position detection sensor 24 (Step S106). When the controller 34 determines that the position of the optical system 21 has reached the target position (Step S106: Yes), the endoscope apparatus 1 ends this process. Conversely, when the controller 34 determines that the position of the optical system 21 has not reached the target position (Step S106: No), the endoscope apparatus 1 returns to Step S102 described above. In this case, the controller 34 repeatedly performs Steps S102 to S104 described above until the position of the optical system 21 has reached the target position.

According to the first embodiment described above, the controller 34 causes the voltage value of the drive signal supplied by the drive circuit 33 to be gradually changed and causes the gradually changed drive signal to be supplied; thus, it is possible to prevent a noise from being superimposed on an image signal.

According to the first embodiment, the controller 34 controls the drive signal supplied by the drive circuit 33 such that the voltage value of the drive signal is changed like a stepwise pulse and a stepwise change falls within a blanking period; thus, it is possible to prevent an edge component as a noise source from being superimposed on an image signal.

Although the controller 34 causes the drive circuit 33 to gradually change the voltage of the supplied drive signal according to the first embodiment, this is not a limitation, and the drive current may be gradually changed.

Next, a second embodiment of the present disclosure is described. An endoscope apparatus according to the second embodiment is different from that in the first embodiment described above in the configuration of a control device and the process performed. Specifically, although the control is performed such that the voltage of the drive signal is gradually changed and output in the vertical blanking period and the output of the drive signal is completed in the vertical blanking period according to the first embodiment described above, the control is performed such that the voltage of the drive signal is gradually increased in each vertical blanking period according to the second embodiment. After the configuration of an endoscope apparatus according to the second embodiment is described, the process performed by the endoscope apparatus according to the second embodiment is described below. The same component as that of the endoscope apparatus 1 according to the first embodiment described above is denoted by the same reference numeral, and detailed description thereof is omitted.

Figure 4:
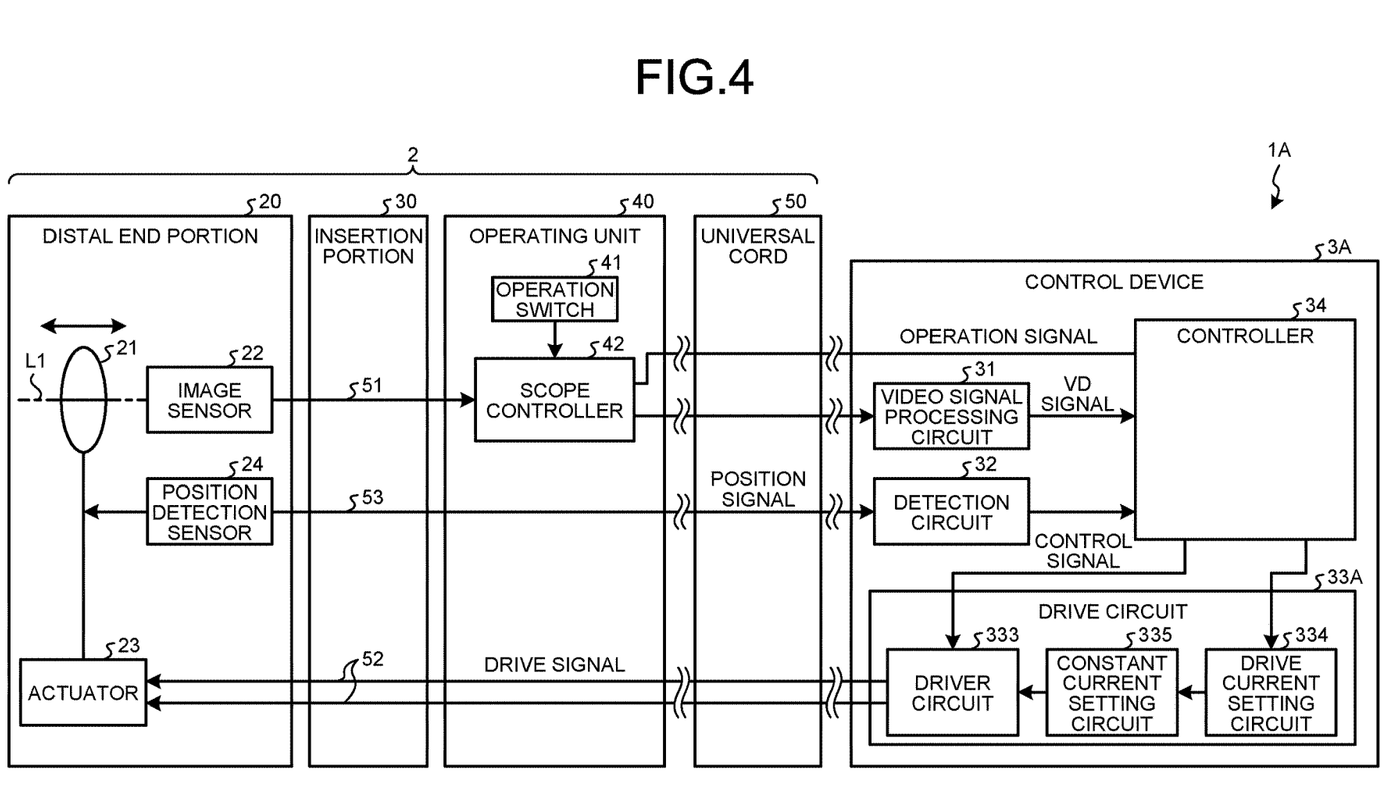
FIG. 4 is a block diagram illustrating a functional configuration of an endoscope apparatus according to a second embodiment.

FIG. 4 is a block diagram illustrating a functional configuration of an endoscope apparatus according to the second embodiment. An endoscope apparatus 1A illustrated in FIG. 4 includes a control device 3A instead of the control device 3 according to the first embodiment described above. The control device 3A includes a drive circuit 33A instead of the drive circuit 33 described above.

The drive circuit 33A supplies the drive signal for driving the actuator 23 provided in the distal end portion 20 of the endoscope 2 under the control of the controller 34. The drive circuit 33A includes the driver circuit 333, a drive current setting circuit 334, and a constant current setting circuit 335.

The drive current setting circuit 334 sets the drive current of the drive signal output from the constant current setting circuit 335 under the control of the controller 34. The drive current setting circuit 334 is configured by using a D/A conversion circuit, a comparator circuit, or the like.

The constant current setting circuit 335 outputs, to the driver circuit 333, the drive signal obtained by adjusting the current of the DC power, which is input from a DC power circuit (not illustrated), to the drive current set by the drive current setting circuit 334.

Figure 5:
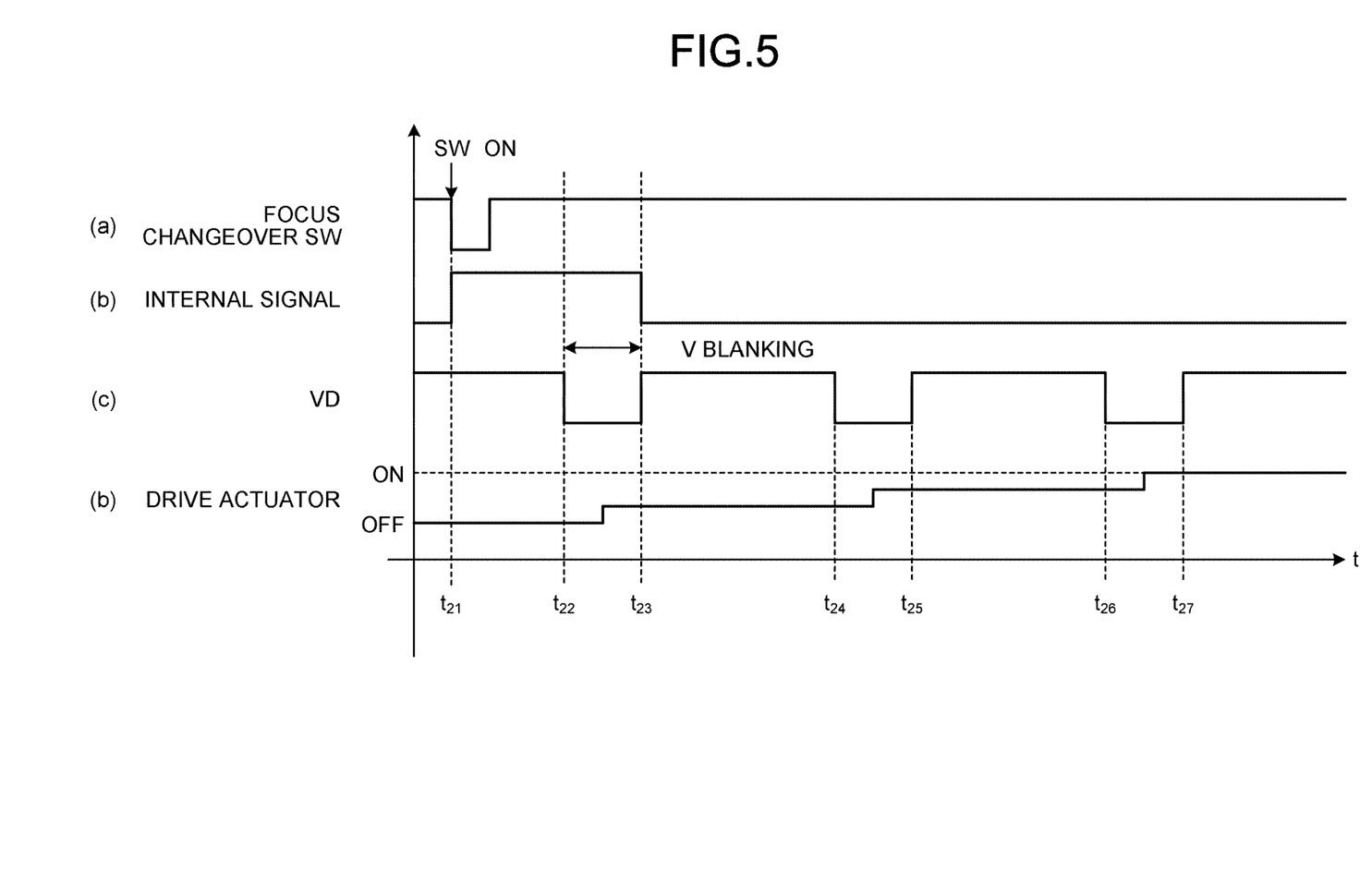
FIG. 5 is a timing chart illustrating an operation performed by the endoscope apparatus according to the second embodiment.

Next, a process performed by the endoscope apparatus 1A is described. FIG. 5 is a timing chart illustrating the overview of an operation performed by the endoscope apparatus 1A. In FIG. 5, (a) denotes the timing when the operation switch 41 is pressed, (b) denotes the output timing of an operation signal, (c) denotes the timing of a vertical synchronization signal (VD), and (d) denotes a change in the drive signal of the actuator 23. In FIG. 5, the horizontal axis represents time.

As illustrated in FIG. 5, to cause the drive circuit 33A to supply the drive signal when an operation signal is input from the operation switch 41 (time $t_{21}$), the controller 34 causes the drive circuit 33A to gradually change the voltage value of the drive signal and supply the gradually changed drive signal in each of blanking periods (for example, from time $t_{22}$ to time $t_{23}$, from time $t_{24}$ to time $t_{25}$, and from time $t_{26}$ to time $t_{27}$). Specifically, to gradually change the voltage value of the drive signal supplied by the drive circuit 33A, the controller 34 causes the drive circuit 33A to supply the drive signal such that one transition period of a gradual change in the drive signal supplied by the drive circuit 33A is completed within a blanking period. Although the controller 34 increases the voltage value of the drive signal supplied by the drive circuit 33A as a gradual change by using a pulse in FIG. 5, the voltage value of the drive signal may be, for example, linearly increased in each blanking period. In a case where the drive signal supplied by the drive circuit 33A has a large absolute value, the controller 34 causes the drive circuit 33A to gradually change the drive signal and supply the gradually changed drive signal; however, in a case where the drive signal supplied by the drive circuit has a small absolute value, the drive circuit 33A may instantaneously change the drive signal to zero.

Figure 6:
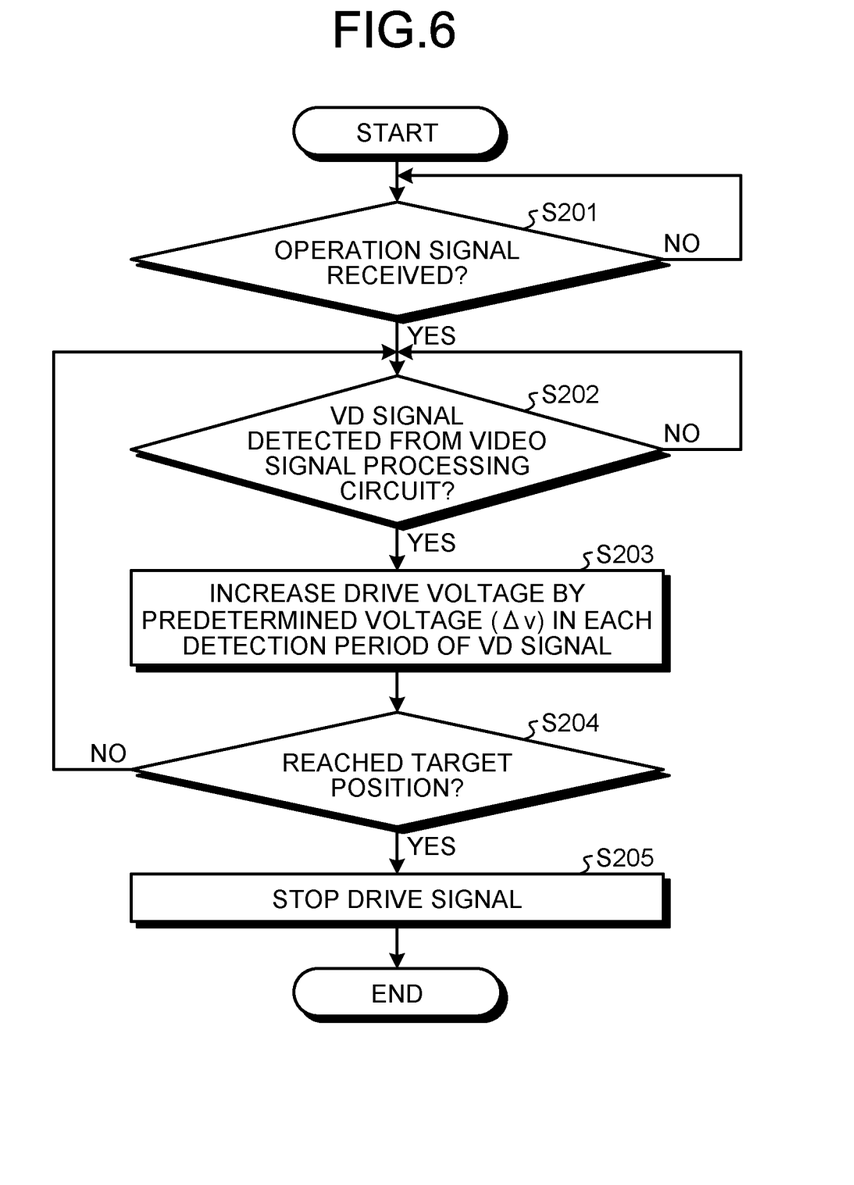
FIG. 6 is a flowchart illustrating the overview of a process performed by the endoscope apparatus according to the second embodiment.

Next, the overview of a process performed by the endoscope apparatus 1A is described. FIG. 6 is a flowchart illustrating the overview of the process performed by the endoscope apparatus 1A. In FIG. 6, Steps S201 and S202 correspond to Steps S101 and S102 in FIG. 3 described above.

At Step S203, the controller 34 causes the drive voltage of the drive signal supplied by the drive circuit 33A to be increased by a predetermined voltage (Δv) and supplied in each detection period of a VD signal. In this case, the controller 34 may cause the drive voltage of the drive signal to be decreased by the predetermined voltage (Δv) when the position of the optical system 21 approaches the target position on the basis of the detection result input from the position detection sensor 24. Specifically, the controller 34 causes the drive voltage to be gradually increased in synchronization with the detection period of the VD signal and causes the drive voltage to be gradually decreased when the position of the optical system 21 approaches the target position so as to cause the optical system 21 to reach the target position. This prevents the position of the optical system 21, which is moved by the actuator 23, from moving beyond the target position.

The controller 34 determines whether the position of the optical system 21 has reached the target position based on the detection result input from the position detection sensor 24 (Step S204). When the controller 34 determines that the position of the optical system 21 has reached the target position (Step S204: Yes), the endoscope apparatus 1 proceeds to Step S205 described below. Conversely, when the controller 34 determines that the position of the optical system 21 has not reached the target position (Step S204: No), the endoscope apparatus 1 returns to Step S202 described above.

At Step S205, the controller 34 stops the drive signal supplied by the drive circuit 33A. After Step S205, the endoscope apparatus 1A ends this process.

According to the second embodiment described above, to cause the drive circuit 33A to supply the drive signal when an operation signal is input from the operation switch 41 (the time $t_{21}$), the controller 34 causes the drive circuit 33A to gradually change the voltage value of the drive signal in each of the blanking periods (for example, from the time $t_{22}$ to the time $t_{23}$, from the time $t_{24}$ to the time $t_{25}$, and from the time $t_{26}$ to the time $t_{27}$) and supply the drive signal; thus, it is possible to prevent a noise from being superimposed on an image signal.

According to the second embodiment, when the controller 34 causes the drive circuit 33A to gradually change the voltage value of the supplied drive signal, the controller 34 causes the drive circuit 33A to supply the drive signal such that one transition period of a gradual change in the drive signal supplied by the drive circuit 33A is completed within a blanking period; thus, it is possible to reduce the power consumption.

Although the controller 34 causes the drive circuit 33A to gradually change the voltage of the supplied drive signal according to the second embodiment, this is not a limitation, and the drive current may be gradually changed.

The components disclosed in the endoscope apparatus according to the first embodiment or the second embodiment of the present disclosure described above may be combined as appropriate to form variations. For example, some components may be deleted from all the components disclosed in the endoscope apparatus according to the first embodiment or the second embodiment of the present disclosure described above. The components disclosed in the endoscope apparatus according to the first embodiment or the second embodiment of the present disclosure described above may be combined as appropriate.

In the endoscope apparatus according to the first embodiment or the second embodiment of the present disclosure, the above-described "unit" may be read as "means", "circuit", or the like. For example, a control unit may be read as a control means or a control circuit.

The program to be executed by the endoscope apparatus according to the first embodiment or the second embodiment of the present disclosure is provided by being recorded in a computer-readable recording medium such as a CD-ROM, a flexible disk (FD), a CD-R, a digital versatile disk (DVD), a USB medium, or a flash memory, in the form of file data installable or executable.

A configuration may be such that the program to be executed by the endoscope apparatus according to the first embodiment or the second embodiment of the present disclosure is stored in a computer connected via a network such as the Internet and is provided by being downloaded via the network.

Although the order of the processes at the steps is described by using expressions such as "first", "subsequently", or "then" in the explanation of the timing chart in this description, the order of the processes necessary for carrying out the present disclosure is not uniquely defined by the expressions. That is, the order of the processes in the timing chart described in this description may be changed to such a degree that there is no contradiction.

Although some of the embodiments of the present application have been described in detail above with reference to the drawings, they are examples, and the present disclosure may be implemented in other modes variously modified or improved based on the knowledge of a person skilled in the art, including the mode described in the field of the disclosure of the present disclosure.

According to the present disclosure, it is possible to prevent a noise from being superimposed on an image signal.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general concept as defined by the appended claims and their equivalents.

What is claimed is:

1. An endoscope apparatus comprising:
   one or more lenses configured to form optical images;
   an image sensor configured to generate image signals in accordance with a predetermined frame rate based on the optical images;
   an actuator configured to move the one or more lenses along an optical axis; and
   a controller comprising:
      a drive circuit configured to feed a drive voltage to the actuator; and
      a processor configured to:
         detect a vertical blanking period of one of the image signals;
         control the drive circuit to gradually increase the drive voltage supplied to the actuator within the vertical blanking period;
         determine whether the drive voltage that has been gradually increased has reached a predetermined drive voltage; and
         in response to determining that the drive voltage has reached the predetermined drive voltage, control the drive circuit to decrease the drive voltage supplied to the actuator.

2. The endoscope apparatus according to claim 1, wherein the processor is configured to:
   receive an operation signal; and
   in response to the operation signal, control the drive circuit to gradually increase the drive voltage supplied to the actuator within the vertical blanking period.

3. The endoscope apparatus according to claim 1, wherein the processor is configured to, in response to determining that the drive voltage has not reached the predetermined drive voltage, determine whether a position of the one or more lenses has reached a target position.

4. The endoscope apparatus according to claim 3, wherein the processor is configured to, in response to determining the position of the one or more lenses has not reached the target position, detect a second vertical blanking period of another of the image signals.

5. A method of controlling an endoscope comprising one or more lenses configured to form optical images, an image sensor configured to generate image signals in accordance with a predetermined frame rate based on the optical images, an actuator configured to move the one or more lenses along an optical axis, and a drive circuit configured to feed a drive voltage to the actuator, the method comprising:
   detecting a vertical blanking period of one of the image signals;
   controlling the drive circuit to gradually increase the drive voltage supplied to the actuator within the vertical blanking period;
   determining whether the drive voltage that has been gradually increased has reached a predetermined drive voltage; and
   in response to determining that the drive voltage has reached the predetermined drive voltage, controlling the drive circuit to decrease the drive voltage supplied to the actuator.

6. The method according to claim 5, comprising:
   receiving an operation signal; and
   in response to the operation signal, controlling the drive circuit to gradually increase the drive voltage supplied to the actuator within the vertical blanking period.

7. The method according to claim 5, comprising:
   in response to determining that the drive voltage has not reached the predetermined drive voltage, determine whether a position of the one or more lenses has reached a target position.

8. The method according to claim 7, comprising:
   in response to determining the position of the one or more lenses has not reached the target position, detecting a second vertical blanking period of another of the image signals.

9. An endoscope apparatus comprising:
   an endoscope distal end portion comprising:
      one or more lenses configured to form optical images;
      an image sensor configured to generate image signals in accordance with a predetermined frame rate based on the optical images; and
      an actuator configured to move the one or more lenses along an optical axis; and
   a controller comprising:
      a drive circuit configured to feed a drive signal to the actuator; and
      a processor configured to:
         detect a vertical blanking period of one of the image signals;
         control the drive circuit to gradually increase the drive signal supplied to the actuator within the vertical blanking period;
         determine whether the drive signal that has been gradually increased has reached a predetermined drive signal;
         in response to determining that the drive signal has not reached the predetermined drive signal, determine whether a position of the one or more lenses has reached a target position; and
         in response to determining the position of the one or more lenses has not reached the target position, detect a second vertical blanking period of another of the image signals.

10. The endoscope apparatus according to claim 9,
wherein the processor is configured to:
- detect vertical blanking periods of two or more of the image signals; and
- control the drive circuit to gradually increase the drive signal supplied to the actuator within each of the vertical blanking periods.

11. The endo scope apparatus according to claim 9, wherein the processor is configured to cause one transition period of a gradual change in the drive signal supplied by the drive circuit to be completed within the vertical blanking period.

12. The endoscope apparatus according to claim 9,
wherein the processor is configured to:
- receive an operation signal; and
- in response to the operation signal, control the drive circuit to gradually increase the drive signal supplied to the actuator within the vertical blanking period.

13. The endoscope apparatus according to claim 9, wherein the processor is configured to, in response to determining that the drive signal has reached the predetermined drive signal, control the drive circuit to gradually decrease the drive signal supplied to the actuator.

* * * * *